United States Patent
Park

(10) Patent No.: US 11,439,328 B2
(45) Date of Patent: Sep. 13, 2022

(54) OPTICAL SENSOR, AND APPARATUS AND METHOD FOR ESTIMATING BIO-INFORMATION

(71) Applicant: SAMSUNG ELECTRONICS CO., LTD., Suwon-si (KR)

(72) Inventor: Moonseong Park, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 222 days.

(21) Appl. No.: 16/740,569

(22) Filed: Jan. 13, 2020

(65) Prior Publication Data

US 2020/0352478 A1 Nov. 12, 2020

(30) Foreign Application Priority Data

May 8, 2019 (KR) .................. 10-2019-0053757

(51) Int. Cl.
*A61B 5/1455* (2006.01)
*A61B 5/145* (2006.01)
*A61B 5/00* (2006.01)

(52) U.S. Cl.
CPC ........ *A61B 5/1455* (2013.01); *A61B 5/14546* (2013.01); *A61B 5/725* (2013.01); *A61B 5/7267* (2013.01); *A61B 5/7278* (2013.01); *A61B 2562/0238* (2013.01); *A61B 2562/043* (2013.01)

(58) Field of Classification Search
CPC ... A61B 5/1455; A61B 5/14546; A61B 5/725; A61B 5/7267; A61B 5/7278; A61B 2562/0238; A61B 2562/043
See application file for complete search history.

(56) References Cited

U.S. PATENT DOCUMENTS

| | | | | |
|---|---|---|---|---|
| 5,348,003 A | * | 9/1994 | Caro | ................. A61B 5/14546 356/39 |
| 5,515,169 A | * | 5/1996 | Cargill | ...................... G01J 3/26 250/226 |
| 7,113,814 B2 | * | 9/2006 | Ward | .................. A61B 5/0071 600/310 |
| 8,384,905 B2 | * | 2/2013 | Wu | ......................... G01J 3/12 356/445 |

(Continued)

FOREIGN PATENT DOCUMENTS

EP       1586854 A2 * 10/2005   ......... G01B 9/02027
KR   10-2012-0049487 A      5/2012

(Continued)

OTHER PUBLICATIONS

Abrisa Technologies, "What is a Dichoric Filter?", 2014 (Year: 2014).*

(Continued)

*Primary Examiner* — David J. McCrosky
*Assistant Examiner* — Clarissa Cuevas
(74) *Attorney, Agent, or Firm* — Sughrue Mion, PLLC

(57) ABSTRACT

An optical sensor according to an example embodiment includes: a light source part configured to emit light onto an object; a signal separator configured to separate optical signals, returning from the object, into a fluorescence signal and a non-fluorescence signal; a first photodetector part configured to detect the non-fluorescence signal; and a second photodetector part configured to detect the fluorescence signal.

17 Claims, 17 Drawing Sheets

(56) References Cited

U.S. PATENT DOCUMENTS

| | | | |
|---|---|---|---|
| 8,476,603 B2* | 7/2013 | Moise | G01N 21/645 250/461.1 |
| 8,901,513 B2 | 12/2014 | Gilmore et al. | |
| 9,037,204 B2* | 5/2015 | Schlottau | A61B 5/14552 600/310 |
| 9,140,648 B2* | 9/2015 | Tokhtuev | G01N 21/59 |
| 10,190,977 B2* | 1/2019 | Marcus | G01N 21/45 |
| 10,952,655 B1* | 3/2021 | Jiao | A61B 5/7271 |
| 2005/0197582 A1 | 9/2005 | Ferguson et al. | |
| 2009/0270702 A1 | 10/2009 | Zeng et al. | |
| 2009/0306521 A1 | 12/2009 | Ermakov et al. | |
| 2010/0179435 A1 | 7/2010 | Sharifzadeh et al. | |
| 2010/0267077 A1 | 10/2010 | Patrice | |
| 2012/0228519 A1 | 9/2012 | Gilmore et al. | |
| 2012/0330164 A1 | 12/2012 | Ermakov et al. | |
| 2013/0041267 A1 | 2/2013 | Ntziachristos et al. | |
| 2013/0289414 A1 | 10/2013 | Adibnazari et al. | |
| 2014/0058224 A1 | 2/2014 | Gellermann et al. | |
| 2015/0123014 A1* | 5/2015 | Palomba | G01N 21/94 250/459.1 |
| 2018/0214040 A1 | 8/2018 | Tognetti et al. | |
| 2020/0046269 A1* | 2/2020 | Park | G01N 21/658 |
| 2021/0033525 A1* | 2/2021 | Campbell | G01N 21/3577 |

FOREIGN PATENT DOCUMENTS

| | | | | |
|---|---|---|---|---|
| KR | 10-2016-0017601 A | | 2/2016 | |
| WO | WO-2018220160 A1 * | 12/2018 | | C09K 11/565 |

OTHER PUBLICATIONS

Gines, "Emission Fingerprinting with Lambda Stacks", 2016 (Year: 2016).*

Nawrot, "A Fluorescent Biosensor for Detection Vital Body Fluid's Agents", 2018 (Year: 2018).*

Barman, "Raman Spectrocopy based sensitive and specific detection of glycated hemoglobin", 2012 (Year: 2012).*

Healthline, What are Flavonoids? Everything you need to know, 2020 (Year: 2020).*

Healthline, Carotenoids: Everything you need to know, 2020 (Year: 2020).*

Gillbro, "Carotenoid fluorescence" Jun. 1989 (Year: 1989).*

Ferrara, "A method for visualizing fluorescence of flavonoid therapeutics in vivo in the model eukaryote Dictyostelium discoideum", Feb. 12, 2019 (Year: 2019).*

* cited by examiner

OPTICAL SENSOR, AND APPARATUS AND METHOD FOR ESTIMATING BIO-INFORMATION

CROSS-REFERENCE TO RELATED APPLICATION(S)

This application claims priority from Korean Patent Application No. 10-2019-0053757, filed on May 8, 2019, in the Korean Intellectual Property Office, the entire disclosure of which is incorporated herein by reference for all purposes.

BACKGROUND

1. Field

Example embodiments of the disclosure relate to detecting a non-fluorescence signal and a fluorescence signal by separating the non-fluorescence signal and the fluorescence signal.

2. Description of the Related Art

Reactive oxygen species are an important part of the biological defense mechanisms, such as white blood cells that protect the body against infections. However, it has been known that excessive production of reactive oxygen species in the body may lead to various diseases in tissues.

Common factors that cause the reactive oxygen species include stress, alcohol, peroxides, medicine, and the like. The reactive oxygen species produced by these factors may cause cranial nerve diseases, circulatory diseases, cancer, digestive tract diseases, liver diseases, arteriosclerosis, renal diseases, diabetes, aging, and the like.

Human bodies have a series of antioxidant defense systems to protect against oxygen toxicity. For normal operation of the systems, it is essential to have sufficient amounts of antioxidants such as vitamin E, vitamin C, carotenoid, flavonoid, ascorbic acid, tocopherol, and the like, and it is important to consume a sufficient amount of foods that are rich in antioxidants for an effective antioxidant action.

The total antioxidant capacity is a comprehensive antioxidant capacity obtained by summation of antioxidant capacities of various antioxidants, and it is important to measure various in vivo antioxidants in order to assess health and life habits of individuals.

SUMMARY

One or more example embodiments provide an optical sensor, which may measure a non-fluorescence signal and a fluorescence signal by separating the non-fluorescence signal and the fluorescence signal, and an apparatus and a method for estimating bio-information using the optical sensor.

According to an aspect of an example embodiment, there is provided an optical sensor, including: a light source part configured to emit light onto an object; a signal separator configured to separate optical signals, returning from the object, into a fluorescence signal and a non-fluorescence signal; a first photodetector part configured to detect the non-fluorescence signal; and a second photodetector part configured to detect the fluorescence signal.

The light source part may include: a light source configured to emit light in a predetermined wavelength range; and a wavelength tunable filter disposed on a light-emitting surface of the light source.

The light source may emit white light.

The light source part may include a plurality of light sources configured to respectively emit light of different wavelengths.

The signal separator may include at least one of a dichroic filter, a beam splitter, a cut-on filter, or a cut-off filter.

The signal separator may include at least one cut-on filter configured to pass an optical signal, having a wavelength greater than a predetermined wavelength, among the optical signals returning from the object; and the second photodetector part may include at least one photodetector configured to detect an optical signal, having passed through each of the at least one cut-on filter, as the fluorescence signal.

The signal separator may include at least one cut-off filter configured to pass an optical signal, having a wavelength less than the predetermined wavelength, among the optical signals returning from the object; and the first photodetector part comprises at least one photodetector configured to detect an optical signal, having passed through the at least one cut-off filter, as the non-fluorescence signal.

The signal separator may include a dichroic filter configured to reflect an optical signal having a wavelength greater than a predetermined wavelength and pass an optical signal having a wavelength less than the predetermined wavelength, among the optical signals returning from the object; the first photodetector part may include at least one first photodetector configured to detect an optical signal, having passed through the dichroic filter, as the non-fluorescence signal; and the second photodetector part may include at least one second photodetector configured to detect an optical signal, having reflected from the dichroic filter, as the fluorescence signal.

The at least one first photodetector may include a horizontal photodetector; and the at least one second photodetector may include a vertical photodetector.

The signal separator may further include a support configured to support the dichroic filter.

The support may support the dichroic filter to have a predetermined slope with respect to a substrate on which the optical sensor is positioned.

The predetermined slope may be determined based on a maximum divergence angle of an optical signal detectable by the first photodetector, and a maximum divergence angle of an optical signal detectable by the second photodetector.

According to an aspect of an example embodiment, there is provided an apparatus for estimating bio-information, the apparatus including: an optical sensor configured to emit light onto an object, configured to separate optical signals, which return from the object, into a fluorescence signal and a non-fluorescence signal, and configured to separately detect the non-fluorescence signal and the fluorescence signal; and a processor configured to estimate at least one of a concentration or an amount of a first analyte in the object by analyzing the detected non-fluorescence signal, and estimate at least one of a concentration or an amount of a second analyte in the object by analyzing the detected fluorescence signal.

The processor may reconstruct a non-fluorescence spectrum based on the detected non-fluorescence signal, and may reconstruct a fluorescence spectrum based on the detected fluorescence signal.

The processor may estimate the at least one of the concentration or the amount of the first analyte and the at least one of the concentration or the amount of the second analyte by using at least one of regression analysis, machine learning, Net Analyte Signal (NAS), or deep learning.

The first analyte may include carotenoid; and the second may include flavonoid.

The processor may estimate at least one a health condition or a life habit of the object based on the estimated at least one of the concentration or the amount of the first analyte and the estimated at least one of the concentration or the amount of the second analyte.

According to an aspect of an example embodiment, there is provided a method of estimating bio-information, the method including: emitting light onto an object; separating optical signals, returning from the object, into a fluorescence signal and a non-fluorescence signal; detecting the non-fluorescence signal; detecting the fluorescence signal; estimating at least one of a concentration or an amount of a first analyte in the object by analyzing the detected non-fluorescence signal; and estimating at least one of a concentration or an amount of a second analyte in the object by analyzing the detected fluorescence signal.

The first analyte may include carotenoid; and the second analyte may include flavonoid.

The method of estimating bio-information may further include estimating at least one of a health condition or a life habit of the object based on the estimated at least one of the concentration or the amount of the first analyte and the estimated at least one of the concentration or the amount of the second analyte.

BRIEF DESCRIPTION OF THE DRAWINGS

The above and/or other aspects of the disclosure will become apparent and more readily appreciated from the following description of the example embodiments, taken in conjunction with the accompanying drawings, in which.

DETAILED DESCRIPTION

Figure 1:
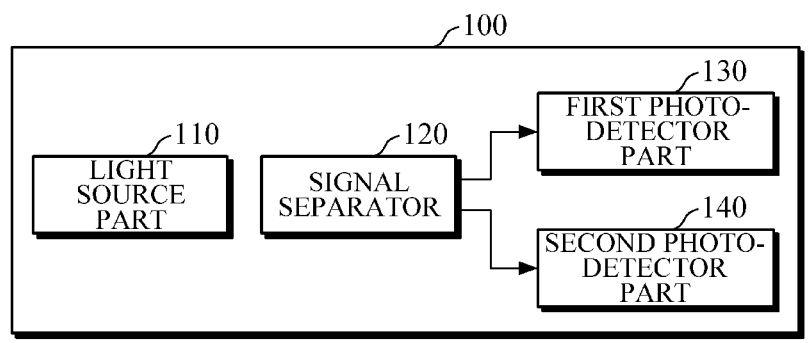
FIG. 1 is a block diagram illustrating an optical sensor according to an example embodiment.

Hereinafter, example embodiments of the disclosure will be described in detail with reference to the accompanying drawings. It should be noted that wherever possible, the same reference symbols refer to same parts even in different drawings. In the following description, a detailed description of known functions and configurations incorporated herein will be omitted when it may obscure the subject matter of the disclosure. Throughout the drawings and the detailed description, unless otherwise described, the same drawing reference numerals will be understood to refer to the same elements, features, and structures. The relative size and depiction of these elements may be exaggerated for clarity, illustration, and convenience.

Process steps described herein may be performed differently from a specified order, even if a specified order is clearly stated in the context of the disclosure. For example, each step may be performed in a specified order, at substantially the same time, or in a reverse order.

Further, the terms used throughout this specification are defined in consideration of the functions according to example embodiments, and may be varied according to a purpose of a user or manager, or precedent and so on. Therefore, definitions of the terms should be made on the basis of the overall context.

It will be understood that, although the terms first, second, etc. may be used herein to describe various elements, these elements should not be limited by these terms. These terms are only used to distinguish one element from another. Any references to singular may include plural unless expressly stated otherwise. In the specification, it should be understood that the terms, such as 'including' or 'having,' etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Further, components that will be described in the specification are discriminated merely according to functions mainly performed by the components. That is, two or more components may be integrated into a single component. Furthermore, a single component may be separated into two or more components. Moreover, each component may additionally perform some or all of a function executed by another component in addition to the main function thereof. Some or all of the main function of each component may be carried out by another component. Each component may be implemented as hardware, software, or a combination of both.

FIG. 1 is a block diagram illustrating an optical sensor 100 according to an example embodiment.

The optical sensor 100 of FIG. 1 is an apparatus which may detect a non-fluorescence signal and a fluorescence signal by separating the non-fluorescence signal and the fluorescence signal, and may be embedded in an electronic device or may be enclosed in a housing to be provided as a separate device. Examples of the electronic device may include a cellular phone, a smartphone, a tablet PC, a laptop computer, a personal digital assistant (PDA), a portable multimedia player (PMP), a navigation, an MP3 player, a digital camera, a wearable device, and the like; and examples of the wearable device may include a wristwatch-type wearable device, a wristband-type wearable device, a ring-type wearable device, a waist belt-type wearable device, a necklace-type wearable device, an ankle band-type wearable device, a thigh band-type wearable device, a forearm band-type wearable device, and the like. However, the electronic device is not limited to the above examples, and the wearable device is neither limited thereto.

Referring to FIG. 1, the optical sensor 100 includes a light source part 110, a signal separator 120, a first photodetector part 130, and a second photodetector part 140.

The light source part 110 may emit light of a predetermined wavelength onto an object. The light of the predetermined wavelength may include visible light and near-infrared light, but is not limited thereto. That is, wavelengths of light to be emitted by the light source part 110 may vary according to the purpose of measurement or the type of an analyte. The light source part 110 is not necessarily a single light source, and may be provided in an array of a plurality of light sources. In the case where the light source part 110 is provided in a plurality of light sources, the plurality of light sources may emit light of different wavelengths or may emit light of the same wavelength. In an example embodiment, examples of the light source part 110 may include a light-emitting body, a lamp, a light emitting diode (LED), a laser diode including an Edge Emitter Laser (EEL) and a Vertical Cavity Surface Emitting Laser (VCSEL), and the like, but the light source part 110 is not limited thereto.

In addition, the light source part 110 may further include at least one optical element (e.g., filter, mirror, etc.) for filtering light emitted by a light source or for directing light emitted by the light source toward a desired position of the object.

The signal separator 120 may separate optical signals, returning from the object, into fluorescence signals and non-fluorescence signals. In an example embodiment, the signal separator 120 may include a dichroic filter, a beam splitter, a cut-on filter, a cut-off filter, and the like, but is not limited thereto.

The first photodetector part 130 may detect the non-fluorescence signal which is separated by the signal separator 120, The first photodetector part 130 is not necessarily a single device, and may be provided in an array of a plurality of devices. In an example embodiment, the first photodetector part 130 may include a photo diode, a photo transistor (PTr), an image sensor (e.g., a charge-coupled device (CCD), a. Complementary Metal Oxide Semiconductor (CMOS), etc.), and the like, but is not limited thereto.

The second photodetector part 140 may detect the fluorescence signal which is separated by the signal separator 120. The second photodetector part 140 is not necessarily a single device, and may be provided in an array of a plurality of devices. In an example embodiment, the second photodetector part 140 may include a photo diode, a photo transistor (PTr), an image sensor (e.g., a charge-coupled device (CCD), a Complementary Metal Oxide Semiconductor (CMOS), etc.), and the like, but is not limited thereto.

The object may be body tissue which may come into contact with the optical sensor 100. For example, the body tissue may be tissue of body parts, including hands, arms, legs, ears, lips, and the like, or tissue extracted from the body parts.

Hereinafter, examples of a structure of the optical sensor 100 will be described in detail with reference to FIGS. 2A to 5B.

Figure 2A:
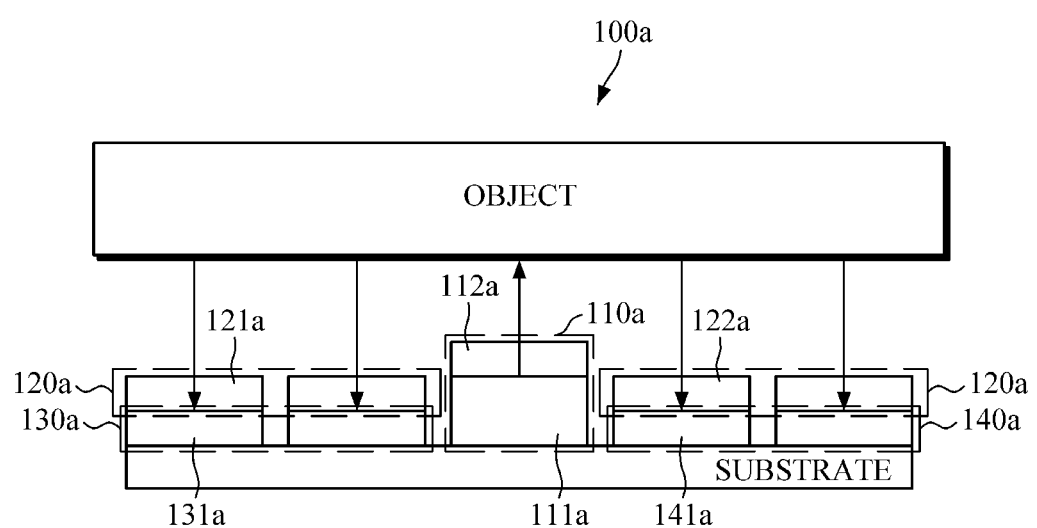
FIGS. 2A and 2B are diagrams illustrating a structure of an optical sensor according to an example embodiment.
Figure 2B:
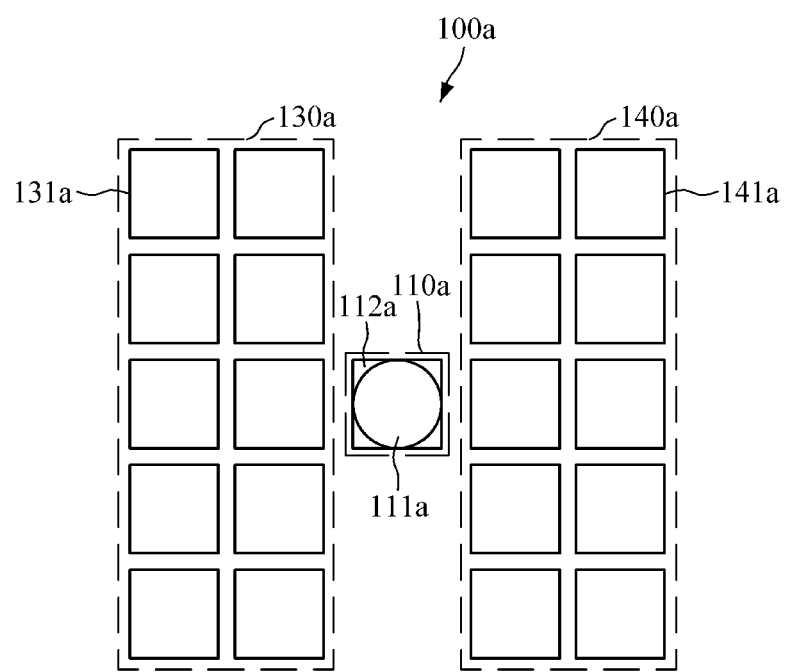

FIGS. 2A and 2B are diagrams illustrating a structure of an optical sensor according to an example embodiment. Specifically, FIG. 2A is a cross-sectional diagram of an optical sensor according to an example embodiment of the disclosure, and FIG. 2B is a plan diagram of an optical sensor according to an example embodiment of the disclosure. An optical sensor 100a illustrated in FIGS. 2A and 2B may be an example of the optical sensor 100 of FIG. 1. For convenience of explanation, a signal separator 120a is not shown in FIG. 2B. Further, FIG. 2B illustrates an example in which 20 photodetectors are included, but this is merely an example, and there is no limitation on the number of the photodetectors.

Referring to FIGS. 2A and 2B, the optical sensor 100a includes a light source part 110a, the signal separator 120a, a first photodetector part 130a, and a second photodetector part 140a.

The light source part 110a may include a light source 111a and a wavelength tunable filter 112a.

The light source 111a is a single light source, and may emit light in a predetermined wavelength range onto an object. Light in the predetermined wavelength range may be white light, but is not limited thereto. The wavelength tunable filter 112a is disposed on a light-emitting surface of the light source 111a, to pass light of a pass wavelength among the emitted light beams. The pass wavelength of the wavelength tunable filter 112a is tunable according to a predetermined control signal.

The signal separator 120a may include one or more first filters 121a and one or more second filters 122a.

The first filter 121a may be a cut-off filter which passes an optical signal having a wavelength less than a first wavelength, among optical signals returning from the object. The second filter 122a may be a cut-on filter which passes an optical signal having a wavelength greater than the first wavelength, among optical signals returning from the object. By considering wavelengths of a non-fluorescence signal and a fluorescence signal of an analyte, the first wavelength may be set to a wavelength, at which a non-fluorescence signal and a fluorescence signal may be separated from each other. For example, in the case where an analyte is an antioxidant (e.g., carotenoid or flavonoid), the first wavelength may be 650 nm, but is not limited thereto.

The first filter 121a may be disposed on a light-incident surface of each photodetector 131a of the first photodetector part 130a, to pass an optical signal, having a wavelength less than the first wavelength among the optical signals returning from the object, e.g., a non-fluorescence signal. Further, the second filter 122a may be disposed on a light-incident surface of each photodetector 141a of the second photodetector part 140a, to pass an optical signal, having a wavelength greater than the first wavelength among the optical signals returning from the object, e.g., a fluorescence signal.

The first photodetector part 130a may include one or more photodetectors 131a, and may detect a non-fluorescence signal having passed through the one or more first filters 121a. Further, the second photodetector part 140a may include one or more photodetectors 141a, and may detect a fluorescence signal having passed through the one or more second filters 122a.

In an example embodiment, as illustrated in FIG. 2, the one or more photodetectors 131a of the first photodetector part 130a and the one or more photodetectors 141a of the second photodetector part 140a may be arranged symmetrically with respect to the light source part 110a, so that absorbance values may have high symmetry. However, the disclosure is not limited thereto.

Generally, a fluorescence signal has a signal value that is much smaller than that of a non-fluorescence signal. Accordingly, in the case where the first photodetector part 130a measures both the non-fluorescence signal and the fluorescence signal, that is, in the case where one or more first filters 121a are not disposed on the light-incident surface of each photodetector 131a of the first photodetector part 130a, a signal value measured by the first photodetector part 130a may be almost similar to a signal value measured in the case where the first photodetector part 130a measures only the non-fluorescence signal. Accordingly, in an example embodiment, the one or more first filters 121a, which are disposed on the light-incident surface of each photodetector 131a of the first photodetector part 130a, may be omitted.

Figure 3A:
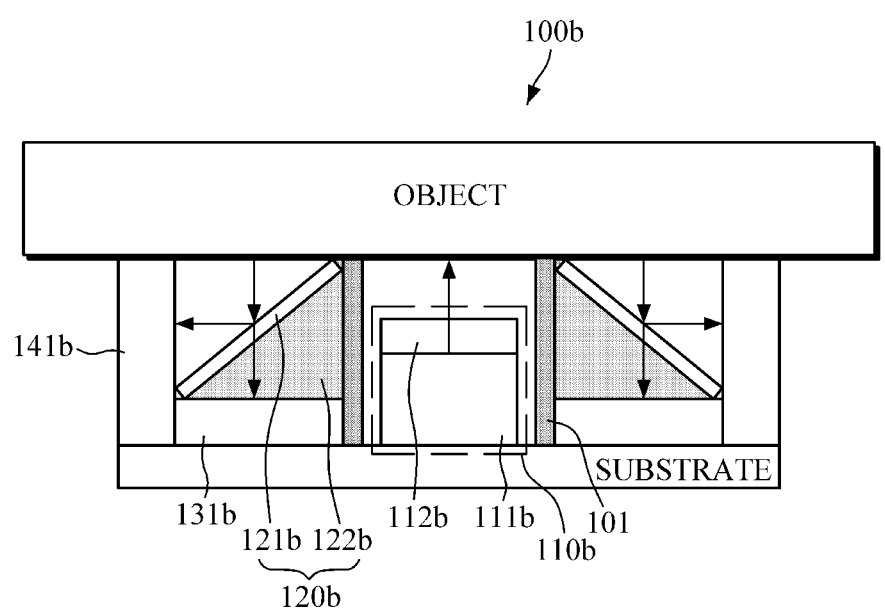
FIGS. 3A and 3B are diagrams illustrating a structure of an optical sensor according to another example embodiment.
Figure 3B:
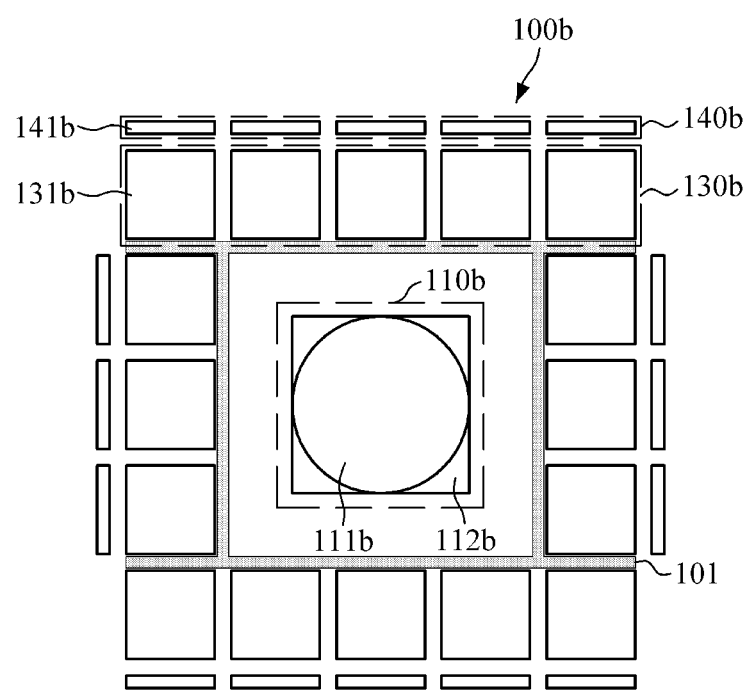

FIGS. 3A and 3B are diagrams illustrating an example of a structure of an optical sensor according to another example embodiment. Specifically, FIG. 3A is a cross-sectional diagram of an optical sensor according to another example embodiment of the disclosure, and FIG. 3B is a plan diagram of an optical sensor according to another example embodiment of the disclosure. An optical sensor 100b illustrated in FIGS. 3A and 3B may be another example of the optical sensor 100 of FIG. 1. For convenience of explanation, a signal separator 120b is not shown in FIG. 3B. Further, FIG. 3B illustrates an example in which 32 photodetectors are included, but this is merely an example, and there is no limitation on the number of the photodetectors. In FIGS. 3A and 3B, a reference numeral 101 may denote a wall for blocking light.

Referring to FIGS. 3A and 3B, the optical sensor 100b includes a light source part 110b, the signal separator 120b, a first photodetector part 130b, and a second photodetector part 140b.

The light source part 110b may include a light source 111b and a wavelength tunable filter 112b. Here, the light source 111b and the wavelength tunable filter 112b are respectively the same as or similar to the light source 111a and the wavelength tunable filter 112a of FIGS. 2A and 2B, and detailed descriptions thereof will be omitted.

The signal separator 120b may include one or more third filters 121b and a support 122b which supports the one or more third filters 121b.

The third filter 121b may be a dichroic filter which passes an optical signal having a wavelength less than a second wavelength and reflects an optical signal having a wavelength greater than the second wavelength, among optical signals returning from an object. By considering wavelengths of non-fluorescence and fluorescence signals of an analyte, the second wavelength may be set to a wavelength, at which a non-fluorescence signal and a fluorescence signal may be separated from each other. For example, in the case where an analyte is an antioxidant (e.g., carotenoid or flavonoid), the second wavelength may be 650 nm, but is not limited thereto. That is, the third filter 121b may pass the non-fluorescence signal and may reflect the fluorescence signal, among optical signals returning from the object.

The support 122b may support the third filter 121b, so that the third filter 121b may have a predetermined slope with respect to a substrate. The predetermined slope may be determined by considering a maximum divergence angle of an optical signal which may be detected by the first photodetector 131b of the first photodetector part 130, and a maximum divergence angle of an optical signal which may be detected by the second photodetector 141b of the second photodetector part 140. The support 122b may include a transparent material so as not to affect light traveling therethrough. For example, the support 122b may have a shape of a prism, a panel, or a bar, but is not limited thereto, and may be modified in various shapes.

The first photodetector part 130b includes one or more first photodetectors 131b, and may measure a non-fluorescence signal having passed through the one or more third filters 121b. Further, the second photodetector part 140b includes one or more second photodetectors 141b, and may measure a fluorescence signal reflected from the one or more third filters 121b. In an example embodiment, the first photodetector 131b may be a horizontal photodetector, and the second photodetector 141b may be a vertical photodetector.

While FIGS. 3A and 3B illustrate an example in which the first photodetector 131b for measuring a non-fluorescence signal is a horizontal photodetector, and the second photodetector 141b is a vertical photodetector, it is also possible that the first photodetector 131b is a vertical photodetector and the second photodetector 141b is a horizontal photodetector. In this case, the third filter 121b may pass an optical signal having a wavelength greater than the second wavelength and may reflect an optical signal having a wavelength less than the second wavelength, among the optical signals returning from the object.

Further, depending on embodiments, instead of the one or more third filters 121b, the signal separator 120b may include one or more beam-splitters, and one or more cut-on filters or cut-off filters which correspond thereto; and the second photodetector 141b may be implemented as a horizontal photodetector and a mirror, instead of a vertical photodetector.

Figure 4A:
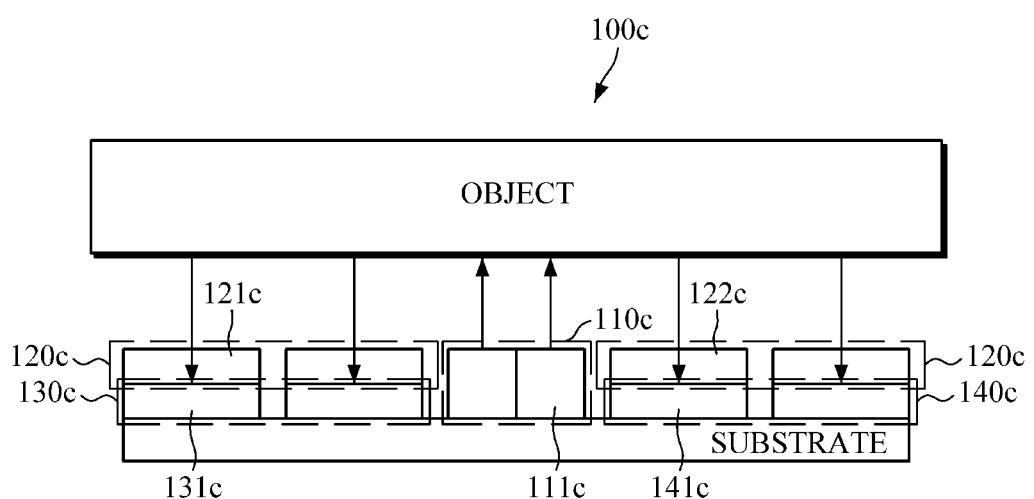
FIGS. 4A and 4B are diagrams illustrating a structure of an optical sensor according to another example embodiment.
Figure 4B:
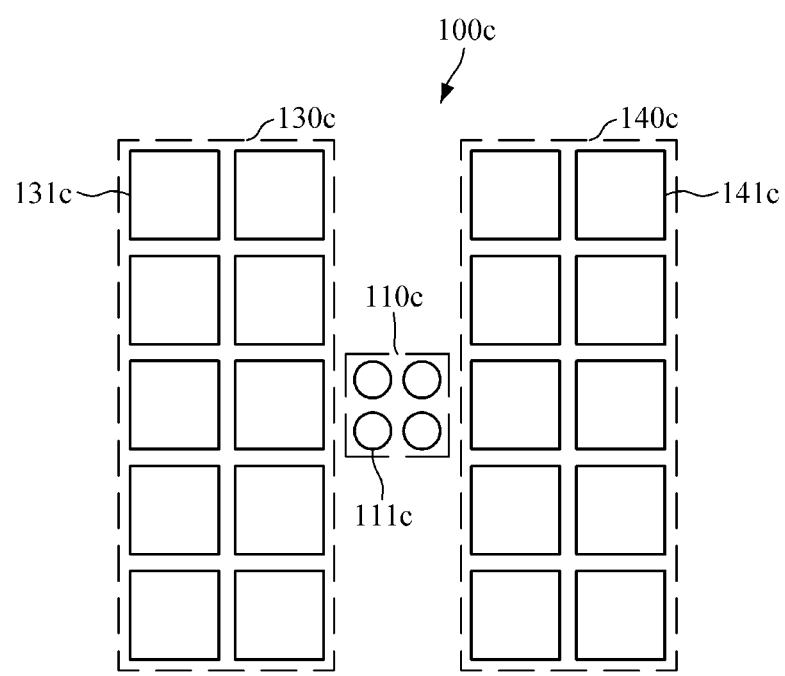

FIGS. 4A and 4B are diagrams illustrating another embodiment of a structure of an optical sensor, Specifically, FIG. 4A is a cross-sectional diagram of an optical sensor according to another embodiment of the disclosure, and FIG. 4B is a plan diagram of an optical sensor according to another embodiment of the disclosure. An optical sensor 100c of FIGS. 4A and 4B may be an example of the optical sensor 100 of FIG. 1. For convenience of explanation, a signal separator 120c is not shown in FIG. 4B Further, FIG. 4B illustrates an example in which 20 photodetectors and four light sources are included, but this is merely an example, and there is no limitation on the number of the photodetectors and the number of the light sources.

Referring to FIGS. 4A and 4B, the optical sensor 100c includes a light source part 110c, the signal separator 120c, a first photodetector part 130c, and a second photodetector part 140c.

The light source part 110c includes a plurality of light sources 111c. The plurality of light sources 111c may emit light of different wavelengths. For example, each of the light sources 111c may emit red light, green light, blue light, near-infrared light, and the like onto an object.

Each light source 111c may be driven in a time-division manner according to a predetermined control signal, to sequentially or simultaneously emit light onto the object. In this case, light source driving conditions, such as an emission time, a driving sequence, a current intensity, a pulse duration, and the like of each light source 111c may be preset. The predetermined control signal may be generated by referring to the light source driving conditions.

The signal separator 120c may include one or more first filters 121c and one or more second filters 122c. Further, the first photodetector part 130c may include one or more photodetectors 131c, and the second photodetector part 140c may include one or more photodetectors 141c. Here, the first filter 121c, the second filter 122c, and the photodetectors 131c and 141c are respectively the same as or similar to the first filter 121a, the second filter 122a, and the photodetectors 131a and 141a of FIGS. 2 and 2B, such that detailed descriptions thereof will be omitted.

In addition, as described above, in an example embodiment, the one or more first filters 121c may be omitted, each of which is disposed on a light-incident surface of each photodetector 131c of the first photodetector part 130c.

Figure 5A:
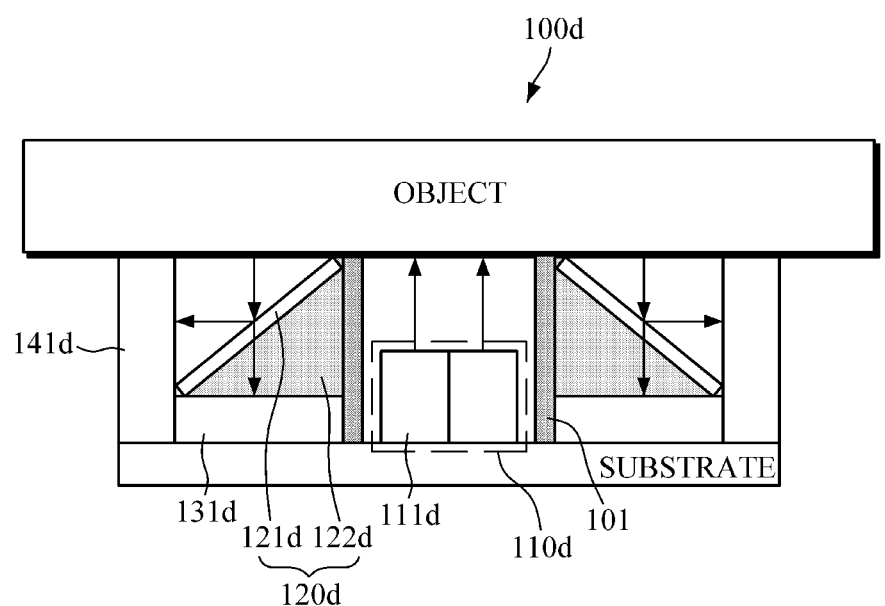
FIGS. 5A and 5B are diagrams illustrating a structure of an optical sensor according to another example embodiment.
Figure 5B:
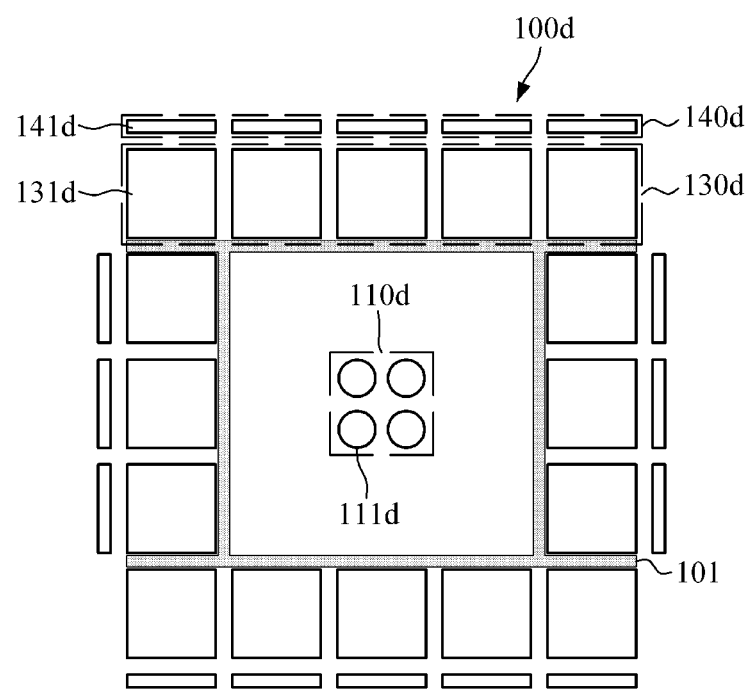

FIGS. 5A and 5B are diagrams illustrating another example embodiment of a structure of an optical sensor.

Specifically, FIG. 5A is a cross-sectional diagram of an optical sensor according to another example embodiment of the disclosure, and FIG. 5B is a plan diagram of an optical sensor according to another example embodiment of the disclosure. An optical sensor 100d of FIGS. 5A and 5B may be an example of the optical sensor 100 of FIG. 1. For convenience of explanation, a signal separator 120d is not shown in FIG. 5B. Further, FIG. 5B illustrates an example in which 32 photodetectors and four light sources are included, but this is merely an example, and there is no limitation on the number of the photodetectors and the number of the light sources. In FIGS. 5A and 5B, a reference numeral 101 may denote a wall for blocking light.

Referring to FIGS. 5A and 5B, the optical sensor 100d includes a light source part 110d, a signal separator 120d, a first photodetector part 130d, and a second photodetector part 140d.

The light source part 110d may include a plurality of light sources 111d and the signal separator 120d may include one or more third filters 121d and a support 122d which supports the one or more third filters 121d. Further, the first photodetector part 130d includes one or more first photodetectors 131d, and the second photodetector part 140d includes one or more second photodetectors 141d. Here, the light source 111d is the same as or similar to the light source 111c of FIGS. 4A and 4B; and the third filter 121d, the support 122d, the first photodetector 131d, and the second photodetector 141d are respectively the same as or similar to the third filter 121b, the support 122b, the first photodetector 131b, and the second photodetector 141b of FIGS. 3A and 3B, such that detailed descriptions thereof will be omitted.

Figure 6:
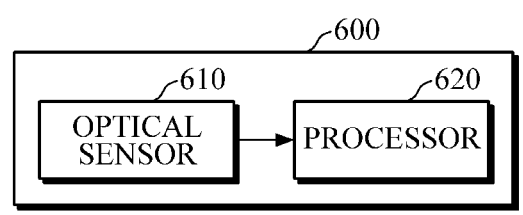
FIG. 6 is a block diagram illustrating an apparatus for estimating bio-information according to an example embodiment.

FIG. 6 is a block diagram illustrating an example of an apparatus 600 for estimating bio-information according to an example embodiment. The apparatus 600 for estimating bio-information of an object is an apparatus for measuring a non-fluorescence signal and a fluorescence signal by separating the signals and estimating bio-information of an object based on the measured signals, and may be embedded in the aforementioned electronic device or may be enclosed in a housing to be provided as a separate device.

Referring to FIG. 6, the apparatus 600 for estimating bio-information includes an optical sensor 610 and a processor 620. Here, the optical sensor 610 may be the optical sensor 100a described above with reference to FIGS. 2A and 2B, or the optical sensor 100b described above with reference to FIGS. 3A and 3B, such that a detailed description of the optical sensor 610 will be omitted.

The processor 620 may control the overall operation of the apparatus 600 for estimating bio-information. The processor 620 may process various signals and operations related to driving the optical sensor 610, estimating the amount (and/or concentration, hereinafter collectively referred to as "amount") of analyte, assessing (or estimating) a health condition and/or life habits, and the like.

The processor 620 may reconstruct a non-fluorescence spectrum and a fluorescence spectrum based on the non-fluorescence signal and the fluorescence signal which are measured by the optical sensor 610. Here, the non-fluorescence spectrum may be an absorption spectrum. However, the disclosure is not limited thereto, and the non-fluorescence spectrum may be a reflectance spectrum or a transmittance spectrum.

For example, by adjusting a pass wavelength of a wavelength tunable filter which is disposed on a light-emitting surface of the light source of the optical sensor 610, the processor 620 may measure the non-fluorescence signal and the fluorescence signal at various wavelengths. Based on the measured non-fluorescence and fluorescence signals, the processor 620 may reconstruct the non-fluorescence spectrum and the fluorescence spectrum using the following Equation 1.

$$y_\alpha = (\alpha E + A^T A)^{-1} A^T p \qquad \text{[Equation 1]}$$

Herein, $\alpha$ denotes a parameter for spectrum reconstruction, E denotes a unit matrix, A denotes a light source spectrum, P denotes the intensity of the optical signal detected by the photodetector, and $y_\alpha$ denotes the reconstructed spectrum. The light source spectrum may refer to a spectrum of light emitted by each light source, and information on the light source spectrum may be pre-stored in an internal or an external database.

The processor 620 may estimate an amount of a first analyte in the object by analyzing the reconstructed non-fluorescence spectrum; and may estimate an amount of a second analyte in the object by analyzing the reconstructed fluorescence spectrum. In this case, the first analyte may include a non-fluorescent substance, such as glucose, triglyceride, urea, uric acid, lactate, protein, cholesterol, ethanol, carotenoid, vitamin, and the like, or a substance which is almost non-fluorescent or minimally fluorescent. The second analyte may include a fluorescent substance, such as protein, vitamin, and flavonoid.

In an example embodiment, the processor 620 may estimate the amount of the first analyte and the amount of the second analyte by using regression analysis (e.g., Classical Least Squares (CLS), Partial Least Squares (PLS), etc.), machine learning (e.g., Artificial Neural Network, Decision Tree, Genetic Algorithm, Genetic Programming, K-Nearest Neighbor, Radial Basis Function Network, Random Forest, Support Vector Machine, etc.), Net Analyte Signal (NAS), deep learning, and the like.

The processor 620 may assess a health condition and/or life habits of an object based on the amount of the first analyte and the amount of the second analyte. Here, the health condition may include disease risk level, antioxidant level, total antioxidant capacity, antioxidant status, blood glucose, skin aging level, skin elasticity, and the like.

Further, depending on embodiments, the processor 620 may estimate the amount of a third analyte more accurately by analyzing the reconstructed non-fluorescence spectrum and the reconstructed fluorescence spectrum. In this case, the third analyte may be a substance other than a non-fluorescent substance, and may include glucose, protein, vitamin, carotenoid, flavonoid, and the like. Further, the processor 620 may assess a health condition and/or life habits of an object based on the estimated amount of the third analyte.

Figure 7:
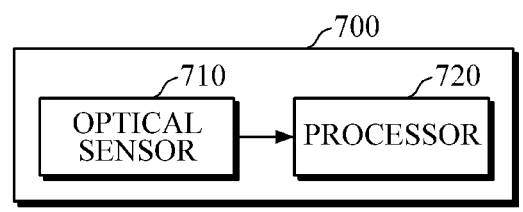
FIG. 7 is a block diagram illustrating an apparatus for estimating bio-information according to another example embodiment.

FIG. 7 is a block diagram illustrating an example of an apparatus 700 for estimating bio-information according to another example embodiment. The apparatus 700 for estimating bio-information of FIG. 7 is an apparatus for measuring a non-fluorescence signal and a fluorescence signal by separating the signals and estimating bio-information of an object based on the measured signals, and may be embedded in the electronic device described above or may be enclosed in a housing to be provided as a separate device.

Refuting to FIG. 7, the apparatus 700 for estimating bio-information includes an optical sensor 710 and a processor 720. Here, the optical sensor 710 may be the optical sensor 100c described above with reference to FIGS. 4A and 4B, or the optical sensor 100d described above with reference to FIGS. 5A and 5B, such that a detailed description of the optical sensor 710 will be omitted.

The processor 720 may control the overall operation of the apparatus 700 for estimating bio-information. The processor 720 may process various signals and operations related to driving the optical sensor 710, estimating the amount of analyte, assessing health condition and/or life habits, and the like.

For example, the processor 720 may measure a non-fluorescence signal and a fluorescence signal at various wavelengths by simultaneously or sequentially driving each light source of the optical sensor 710 according to predetermined driving conditions of the light sources.

The processor 720 may estimate an amount of a first analyte by analyzing the measured non-fluorescence signal; and may estimate an amount of a second analyte by analyzing the measured fluorescence signal. In an example embodiment, the processor 720 may estimate the amount of the first analyte and the amount of the second analyte by using regression analysis, machine learning, Net Analyte Signal (NAS), deep learning, and the like.

In an example embodiment, the processor 720 may assess a health condition and/or life habits of an object based on the amount of the first analyte and the amount of the second analyte.

Further, depending on embodiments, the processor 720 may estimate the amount of a third analyte more accurately by analyzing the measured non-fluorescence and fluorescence signals, and may assess a health condition and/or life habits of an object based on the estimated amount of the third analyte.

Figure 8:
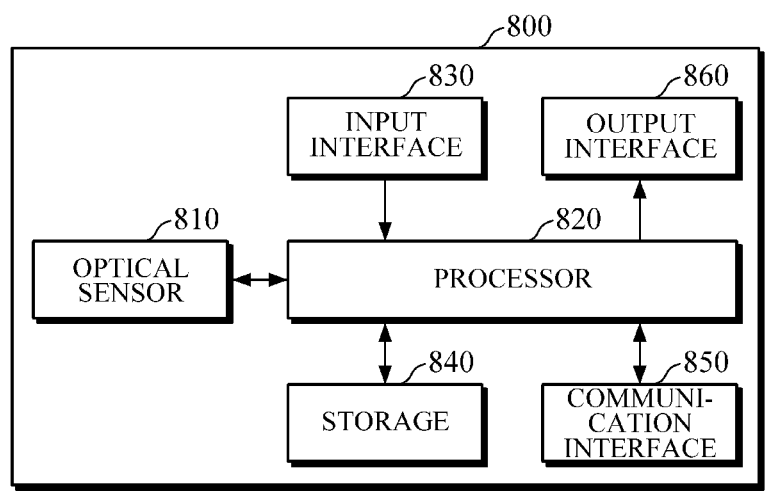
FIG. 8 is a block diagram illustrating an apparatus for estimating bio-information according to another example embodiment.

FIG. 8 is a block diagram illustrating an example of an apparatus 800 for estimating bio-information according to another example embodiment. The apparatus 800 for estimating bio-information of FIG. 8 is an apparatus for measuring a non-fluorescence signal and a fluorescence signal by separating the signals and estimating bio-information of an object based on the measured signals, and may be embedded in the aforementioned electronic device or may be enclosed in a housing to be provided as a separate device.

Referring to FIG. 8, the apparatus 800 for estimating bio-information includes an optical sensor 810, a processor 820, an input interface 830, a storage 840, a communication interface 850, and an output interface 860. Here, the optical sensor 810 and the processor 820 are respectively the same as or similar to the optical sensor 610 and the processor 620 of FIG. 6 or the optical sensor 710 and the processor 720 of FIG. 7, such that detailed descriptions of the optical sensor 810 and the processor 820 will be omitted.

The input interface 830 may receive an input of various operation signals from a user. In an example embodiment, the input interface 830 may include a keypad, a dome switch, a touch pad (e.g., of static pressure and/or capacitance type), a jog wheel, a jog switch, a hardware (H/W) button, and the like. The touch pad, which forms a layer structure with a display, may be called a touch screen.

The storage 840 may store programs or commands for operation of the apparatus 800 for estimating bio-information, and may store data input to the apparatus 800 for estimating bio-information, data measured and processed by the apparatus 800 for estimating bio-information, and the like. The storage 840 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like. Further, the apparatus 800 for estimating bio-information may operate an external storage medium, such as web storage and the like, which performs a storage function of the storage 840 on the Internet.

The communication interface 850 may perform communication with an external device. For example, the communication interface 850 may transmit, to the external device, data input to and stored in the apparatus 800 for estimating bio-information, data measured and processed by the apparatus 800 for estimating bio-information, and the like; or may receive, from the external device, various data related to estimating bio-information.

The external device may be medical equipment using the data input to and stored in the apparatus 800 for estimating bio-information, the data measured and processed by the apparatus 800 for estimating bio-information, and the like, a printer to print out results, or a display to display the results. In addition, the external device may be a digital TV, a desktop computer, a cellular phone, a smartphone, a tablet PC, a laptop computer, a personal digital assistant (PDA), a portable multimedia player (PMP), a navigation, an MP3 player, a digital camera, a wearable device, and the like, but the external device is not limited thereto.

The communication interface 850 may communicate with an external device by using Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, this is merely an example and the disclosure is not limited thereto.

The output interface 860 may output the data input to and stored in the apparatus 800 for estimating bio-information, the data measured and processed by the apparatus 800 for estimating bio-information, and the like. In an example embodiment, the output interface 860 may output the data input to and stored in the apparatus 800 for estimating bio-information, the data measured and processed by the apparatus 800 for estimating bio-information, and the like by using at least one of an acoustic method, a visual method, and a tactile method. To this end, the output interface 860 may include a display, a speaker, a vibrator, and the like.

Figure 9:
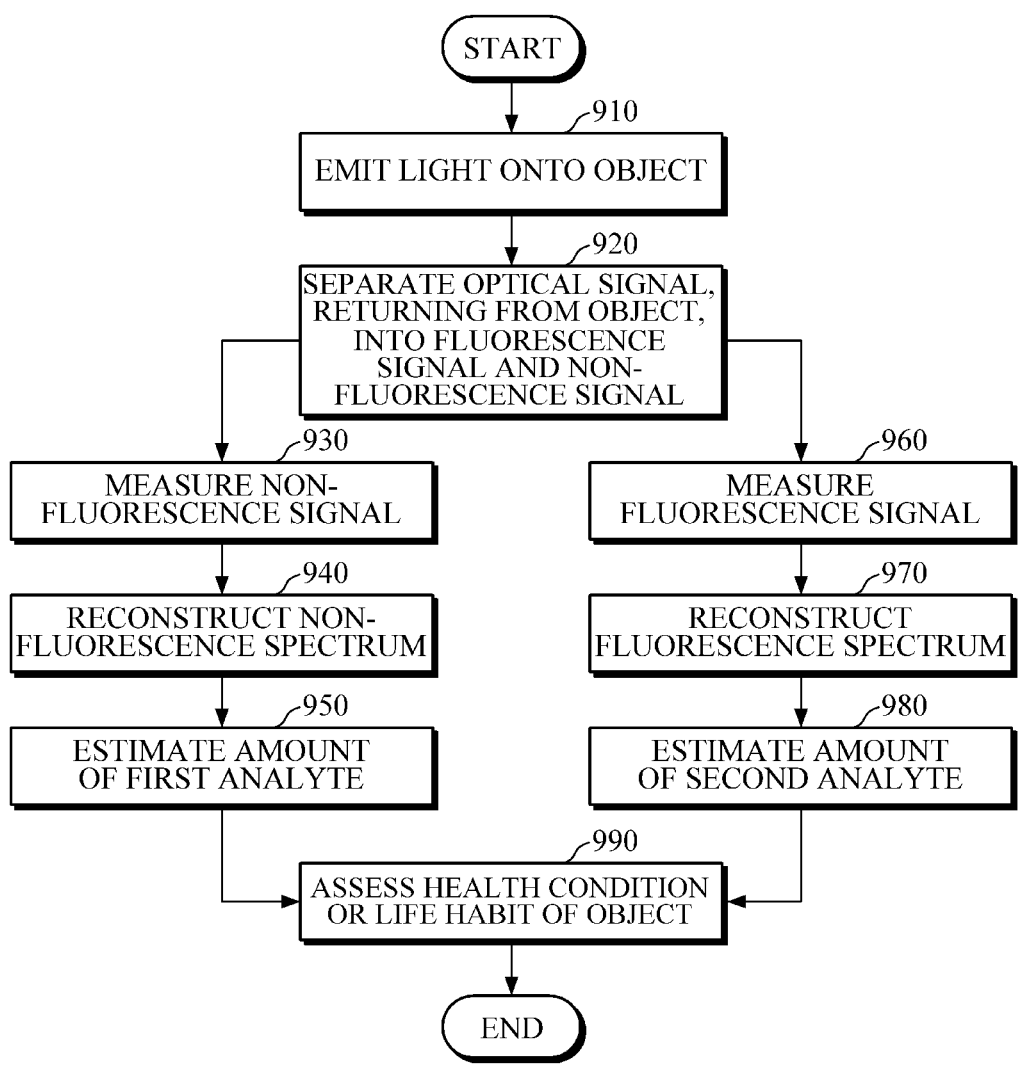
FIG. 9 is a flowchart illustrating a method of estimating bio-information according to an example embodiment.

FIG. 9 is a flowchart illustrating an example of a method of estimating bio-information according to an example embodiment. The method of estimating bio-information of FIG. 9 may be performed by the apparatus 600 for estimating bio-information of FIG. 6.

Referring to FIG. 9, the apparatus for estimating bio-information may emit light onto an object in 910. For example, the apparatus for estimating bio-information may emit light of various wavelengths by adjusting a pass wavelength of a wavelength tunable filter which is disposed on a light-emitting surface of a single light source.

The apparatus for estimating bio-information may separate optical signals, returning from the object, into a fluorescence signal and a non-fluorescence signal in 920.

The apparatus for estimating bio-information may measure the separated non-fluorescence signal in 930, and may reconstruct a non-fluorescence spectrum based on the measured non-fluorescence signal in 940. Here, the non-fluorescence spectrum may be an absorption spectrum, but is not limited thereto, and may be a reflectance spectrum or a transmittance spectrum. For example, based on the measured non-fluorescence signal, the apparatus for estimating bio-information may reconstruct the non-fluorescence spectrum using Equation 1.

The apparatus for estimating bio-information may estimate an amount of a first analyte by analyzing the reconstructed non-fluorescence spectrum in 950. For example, by analyzing the reconstructed non-fluorescence spectrum using regression analysis, machine learning, Net Analyte Signal (NAS), deep learning, and the like, the apparatus for estimating bio-information may estimate the amount of the first analyte.

The apparatus for estimating bio-information may measure the separated fluorescence signal in 960, and may reconstruct a fluorescence spectrum based on the measured fluorescence signal in 970. For example, based on the measured fluorescence signal, the apparatus for estimating bio-information may reconstruct the fluorescence spectrum using Equation 1.

The apparatus for estimating bio-information may estimate an amount of a second analyte by analyzing the reconstructed fluorescence spectrum in 980. For example, by analyzing the reconstructed fluorescence spectrum using regression analysis, machine learning, Net Analyte Signal (NAS), deep learning, and the like, the apparatus for estimating bio-information may estimate the amount of the second analyte.

The apparatus for estimating bio-information may assess a health condition and/or life habits of an object based on the amount of the first analyte and the amount of the second analyte in 990.

Figure 10:
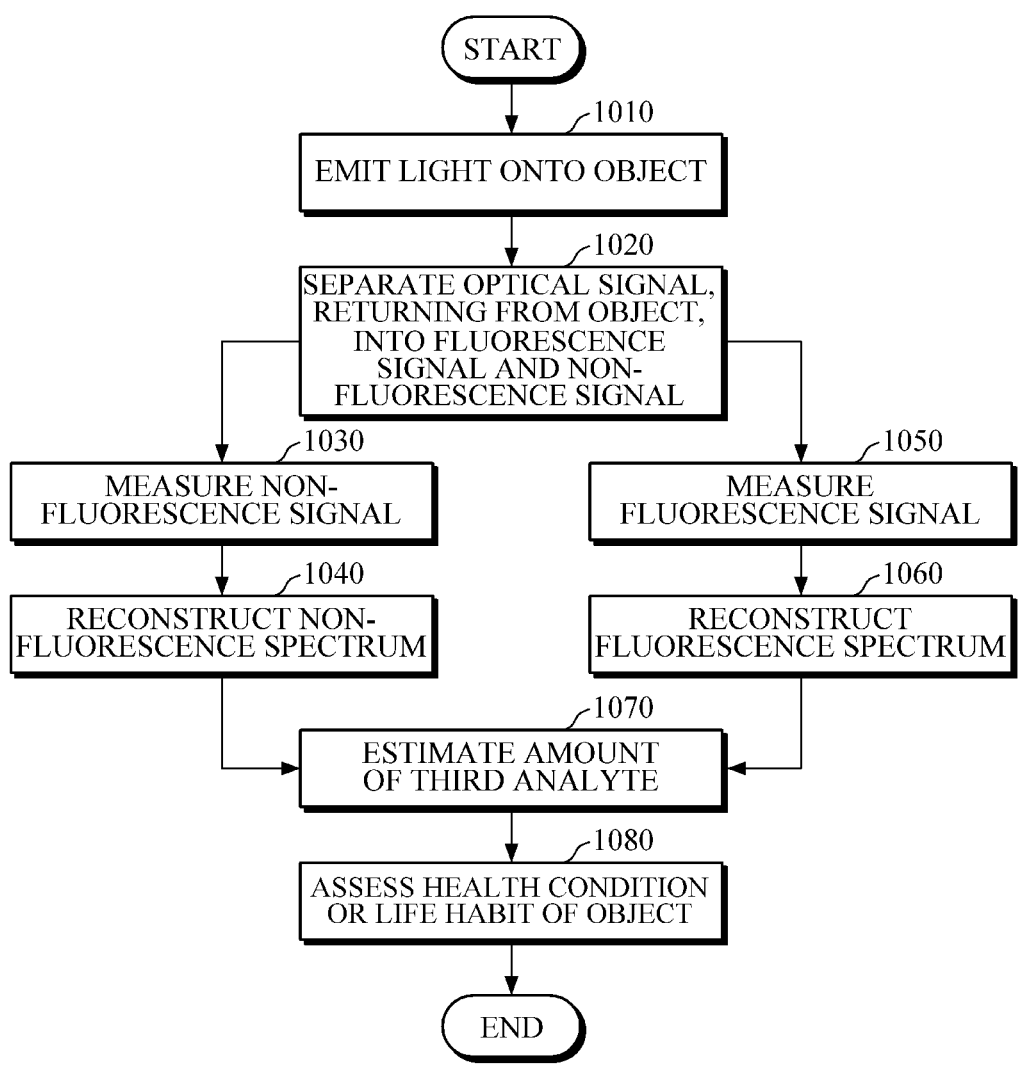
FIG. 10 is a flowchart illustrating a method of estimating bio-information according to another example embodiment.

FIG. 10 is a flowchart illustrating an example of a method of estimating bio-information according to another example embodiment. The method of estimating bio-information of FIG. 10 may be performed by the apparatus 600 for estimating bio-information of FIG. 6.

Referring to FIG. 10, the apparatus for estimating bio-information may emit light onto an object in 1010. For example, the apparatus for estimating bio-information may emit light of various wavelengths onto an object by adjusting a pass wavelength of a wavelength tunable filter which is disposed on a light-emitting surface of a single light source.

The apparatus for estimating bio-information separate optical signals, returning from the object, into a fluorescence signal and a non-fluorescence signal in 1020.

The apparatus for estimating bio-information may measure the separated non-fluorescence signal in 1030, and may reconstruct a non-fluorescence spectrum based on the measured non-fluorescence signal in 1040.

The apparatus for estimating bio-information may measure the separated fluorescence signal in 1050, and may reconstruct a fluorescence spectrum based on the measured fluorescence signal in 1060.

The apparatus for estimating bio-information may estimate an amount of a third analyte by analyzing the reconstructed non-fluorescence spectrum and the reconstructed fluorescence spectrum in 1070, and may assess a health condition and/or life habits of an object based on the estimated amount of the third analyte in 1080.

Figure 11:
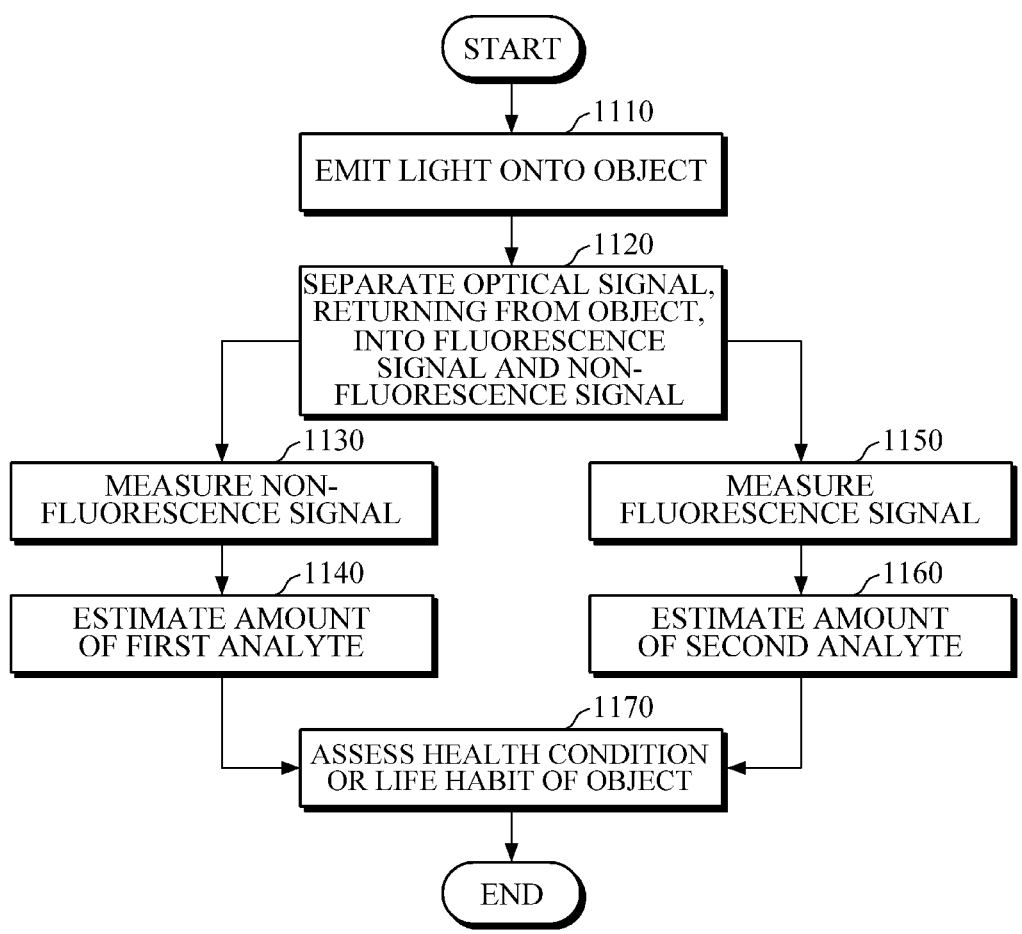
FIG. 11 is a flowchart illustrating a method of estimating bio-information according to another example embodiment.

FIG. 11 is a flowchart illustrating an example of a method of estimating bio-information according to another example embodiment. The method of estimating bio-information of FIG. 11 may be performed by the apparatus 700 for estimating bio-information of FIG. 7.

Referring to FIG. 11, the apparatus for estimating bio-information may emit light onto an object in 1110. For example, the apparatus for estimating bio-information may emit light of various wavelengths by simultaneously or sequentially driving a plurality of light sources according to driving conditions of each light source.

The apparatus for estimating bio-information may separate optical signals, returning from the object, into a fluorescence signal and a non-fluorescence signal in 1120.

The apparatus for estimating bio-information may measure the separated non-fluorescence signal in 1130, and may estimate an amount of a first analyte by analyzing the measured non-fluorescence signal in 1140. For example, by analyzing the non-fluorescence signal using regression analysis, machine learning, Net Analyte Signal (NAS), deep learning, and the like, the apparatus for estimating bio-information may estimate the amount of the first analyte.

The apparatus for estimating bio-information may measure the separated fluorescence signal in 1150, and may estimate an amount of a second analyte by analyzing the measured fluorescence signal in 1160. For example, by analyzing the measured fluorescence signal using regression analysis, machine learning, Net Analyte Signal (NAS), deep learning, and the like, the apparatus for estimating bio-information may estimate the amount of the second analyte.

The apparatus for estimating bio-information may assess a health condition and/or life habits of an object based on the amount of the first analyte and the amount of the second analyte in 1170.

Figure 12:
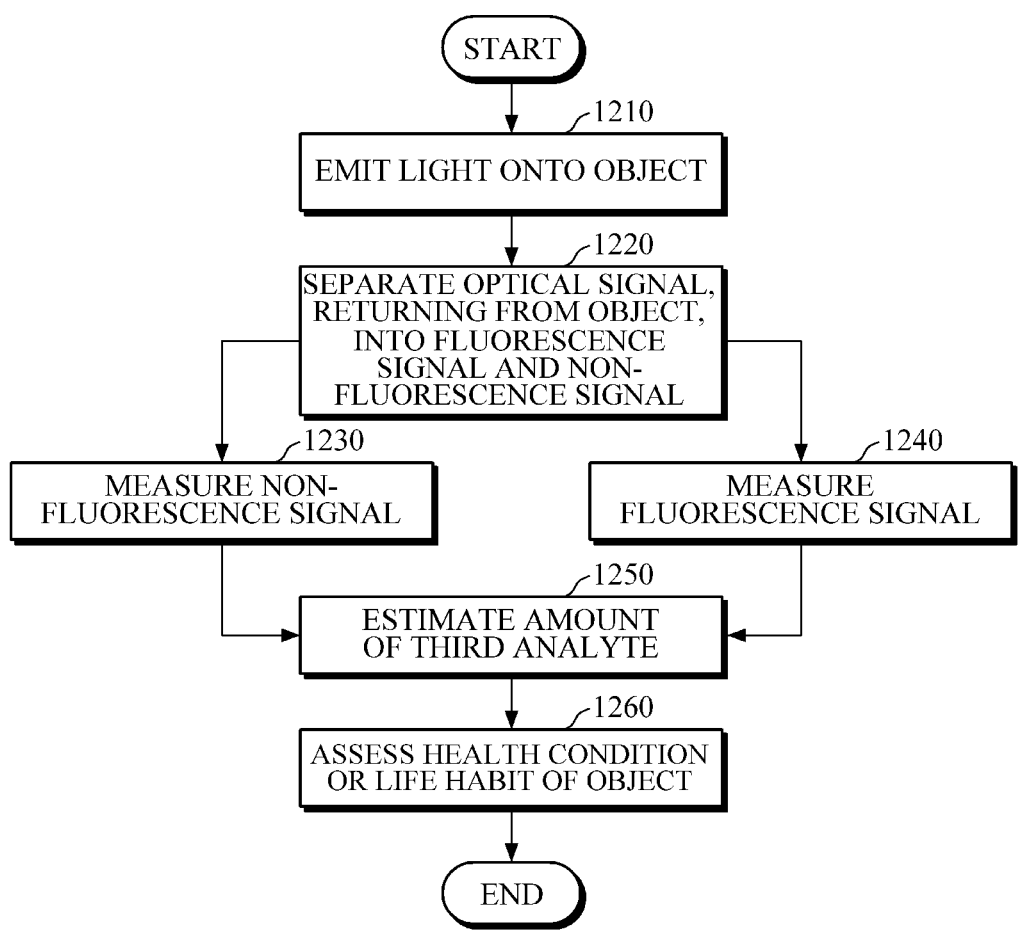
FIG. 12 is a flowchart illustrating a method of estimating bio-information according to another example embodiment.

FIG. 12 is a flowchart illustrating still ano example of a method of estimating bio-information according to another example embodiment. The method of estimating bio-information of FIG. 12 may be performed by the apparatus 700 for estimating bio-information of FIG. 7.

Referring to FIG. 12, the apparatus for estimating bio-information may emit light onto an object in 1210. For example, the apparatus for estimating bio-information may emit light of various wavelengths onto an object by simultaneously or sequentially driving a plurality of light sources according to driving conditions of each light source.

The apparatus for estimating bio-information may separate optical signals, returning from the object, into a fluorescence signal and a non-fluorescence signal in 1220.

The apparatus for estimating bio-information may measure the separated non-fluorescence signal in 1230, and may measure the separated fluorescence signal in 1240.

The apparatus for estimating bio-information may estimate an amount of a third analyte by analyzing the measured non-fluorescence signal and the measured fluorescence signal in 1250, and may assess a health condition and/or life habits of the object based on the estimated amount of the third analyte in 1260.

Figure 13:
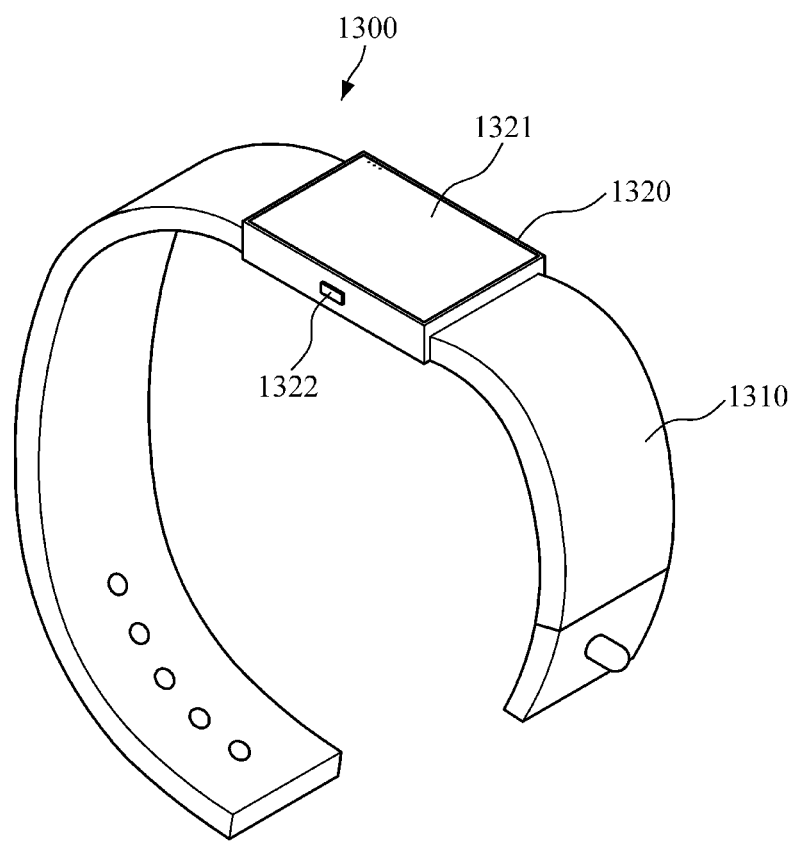
FIG. 13 is a diagram illustrating a wrist-type wearable device according to an example embodiment.

FIG. 13 is a diagram illustrating an example of a wrist-type wearable device.

Referring to FIG. 13, the wrist-type wearable device 1300 includes a strap 1310 and a main body 1320.

The strap 1310 may be connected to both ends of the main body 1320 so as to be fastened in a detachable manner or may be integrally formed therewith as a smart band. The strap 1310 may include a flexible material to be wrapped around a user's wrist so that the main body 1320 may be worn on the wrist.

The main body 1320 may include the apparatuses 600, 700, and 800 for estimating bio-information described above. Further, the main body 1320 may include a battery which supplies power to the wrist-type wearable device 1300 and the apparatuses 600, 700, and 800 for estimating bio-information.

An optical sensor may be mounted at the bottom of the main body 1320 to be exposed to a user's waist. Accordingly, when a user wears the wrist-type wearable device 1300, the optical sensor may naturally come into contact with the user's skin. In this case, the optical sensor may emit light onto an object, and may separate optical signals, returning from the object, into a non-fluorescence signal and a fluorescence signal to measure the non-fluorescence signal and the fluorescence signal separately.

The wrist-type wearable device 1300 may further include a display 1321 and an input interface 1322 which are mounted at the main body 1320. The display 1321 may display data processed by the wrist-type wearable device 1300 and the apparatuses 600, 700 and 800 for estimating bio-information, processing result data hereof, and the like. The input interface 1322 may receive various operation signals from a user.

The disclosure can be realized as a computer-readable code written on a computer-readable recording medium. The computer-readable recording medium may be any type of recording device in which data is stored in a computer-readable manner. Examples of the computer-readable recording medium include a ROM, a RAM, a CD-ROM, a magnetic tape, a floppy disc, an optical disk, and the like. Further, the computer-readable recording medium can be distributed over a plurality of computer systems connected to a network so that a computer-readable recording medium is written thereto and executed therefrom in a decentralized manner.

At least one of the components, elements, modules or units described herein may be embodied as various numbers of hardware, software and/or firmware structures that execute respective functions described above, according to an example embodiment. For example, at least one of these components, elements or units may use a direct circuit structure, such as a memory, a processor, a logic circuit, a look-up table, etc. that may execute the respective functions through controls of one or more microprocessors or other control apparatuses. Also, at least one of these components, elements or units may be specifically embodied by a module, a program, or a part of code, which contains one or more executable instructions for performing specified logic functions, and executed by one or more microprocessors or other control apparatuses. Also, at least one of these components, elements or units may further include or implemented by a processor such as a central processing unit (CPU) that performs the respective functions, a microprocessor, or the like. Two or more of these components, elements or units may be combined into one single component, element or unit which performs all operations or functions of the combined two or more components, elements of units. Also, at least part of functions of at least one of these components, elements or units may be performed by another of these components, element or units. Further, although a bus is not illustrated in the block diagrams, communication between the components, elements or units may be performed through the bus. Functional aspects of the above example embodiments may be implemented in algorithms that execute on one or more processors. Furthermore, the components, elements or units represented by a block or processing steps may employ any number of related art techniques for electronics configuration, signal processing and/or control, data processing and the like.

While a few example embodiments have been described above, the scope of the disclosure is not limited thereto and various modifications and improvements made by those of ordinary skill in the art to concepts defined in the following claims should be understood to fall within the scope of the disclosure.

What is claimed is:

1. An optical sensor comprising:
   a light source part provided on a substrate extending in a first direction, and configured to emit light onto an object toward a second direction, the second direction crossing the first direction;
   a signal separator configured to separate optical signals, returning from the object, into a fluorescence signal and a non-fluorescence signal;
   a wall provided on the substrate, the wall being positioned between the light source part and the signal separator and extending in the second direction;
   a first photodetector part configured to detect the non-fluorescence signal; and
   a second photodetector part configured to detect the fluorescence signal,
   wherein the signal separator comprises a dichroic filter configured to reflect an optical signal having a wavelength greater than a second wavelength and pass an optical signal having a wavelength less than the second wavelength, among the optical signals returning from the object,
   wherein the first photodetector part comprises at least one first photodetector configured to detect the optical signal, that is passed through the dichroic filter, as the non-fluorescence signal, the at least one first photodetector being a horizontal photodetector and extending in the first direction, the horizontal photodetector being provided on the substrate and contacting the wall,
   wherein the second photodetector part comprises at least one second photodetector configured to detect the optical signal, that is reflected from the dichroic filter, as the fluorescence signal, the at least one second photodetector being a vertical photodetector and extending in the second direction, and
   wherein the signal separator further comprises a support configured to support the dichroic filter, the support being positioned between the dichroic filter and the wall and positioned on the horizontal photodetector.

2. The optical sensor of claim 1, wherein the light source part comprises:
   a light source configured to emit light in a predetermined wavelength range; and
   a wavelength tunable filter disposed on a light-emitting surface of the light source.

3. The optical sensor of claim 2, wherein the light source is a single light source configured to emit light in the predetermined wavelength range.

4. The optical sensor of claim 1, wherein the light source part comprises a plurality of light sources configured to respectively emit light of different wavelengths.

5. The optical sensor of claim 1, wherein the signal separator further comprises at least one of a beam splitter, a cut-on filter, or a cut-off filter.

6. The optical sensor of claim 1, wherein the signal separator further comprises at least one first cut-on filter configured to pass an optical signal, having a wavelength greater than a first wavelength, among the optical signals returning from the object; and
   the second photodetector part comprises at least one third photodetector configured to detect the optical signal, that is passed through the at least one first cut-on filter, as the fluorescence signal.

7. The optical sensor of claim 6, wherein the signal separator further comprises at least one second cut-off filter configured to pass an optical signal, having a wavelength less than the first wavelength, among the optical signals returning from the object; and the first photodetector part comprises at least one fourth photodetector configured to detect the optical signal, that is passed through the at least one second cut-off filter, as the non-fluorescence signal.

8. The optical sensor of claim 1, wherein the support is configured to support the dichroic filter to have a predetermined slope with respect to the substrate on which the light source part is positioned.

9. The optical sensor of claim 8, wherein the predetermined slope is determined based on a maximum divergence angle of an optical signal detectable by the at least one first photodetector, and a maximum divergence angle of an optical signal detectable by the at least one second photodetector.

10. An apparatus for estimating bio-information, the apparatus comprising:

an optical sensor configured to emit, by using a light source part provided on a substrate extending in a first direction, light onto an object toward a second direction, the second direction crossing the first direction; configured to separate, by using a signal separator, optical signals, which return from the object, into a fluorescence signal and a non-fluorescence signal; and configured to separately detect the non-fluorescence signal and the fluorescence signal; and a processor configured to estimate at least one of a concentration or an amount of a first analyte in the object by analyzing the detected non-fluorescence signal, and estimate at least one of a concentration or an amount of a second analyte in the object by analyzing the detected fluorescence signal, wherein the signal separator comprises a dichroic filter configured to reflect an optical signal having a wavelength greater than a predetermined wavelength and pass an optical signal having a wavelength less than the predetermined wavelength, among the optical signals returning from the object, wherein the optical sensor comprises:

a wall provided on the substrate, the wall being positioned between the light source part and the signal separator and extending in the second direction;

at least one first photodetector configured to detect the optical signal, that is passed through the dichroic filter, as the non-fluorescence signal, the at least one first photodetector being a horizontal photodetector and extending in the first direction, the horizontal photodetector being provided on the substrate and contacting the wall; and at least one second photodetector configured to detect the optical signal, that is reflected from the dichroic filter, as the fluorescence signal, the at least one second photodetector being a vertical photodetector and extending in the second direction, and wherein the signal separator further comprises a support configured to support the dichroic filter, the support being positioned between the dichroic filter and the wall and positioned on the horizontal photodetector.

11. The apparatus of claim 10, wherein the processor is further configured to reconstruct a non-fluorescence spectrum based on the detected non-fluorescence signal, and configured to reconstruct a fluorescence spectrum based on the detected fluorescence signal.

12. The apparatus of claim 10, wherein the processor is further configured to estimate the at least one of the concentration or the amount of the first analyte and the at least one of the concentration or the amount of the second analyte by using at least one of regression analysis, machine learning, Net Analyte Signal (NAS), or deep learning.

13. The apparatus of claim 10, wherein the first analyte comprises carotenoid;

and the second analyte comprises flavonoid.

14. The apparatus of claim 10, wherein the processor is further configured to estimate at least one of a health condition or a life habit of the object based on the estimated at least one of the concentration or the amount of the first analyte and the estimated at least one of the concentration or the amount of the second analyte.

15. A method of estimating bio-information, the method comprising:

emitting, by using a light source part provided on a substrate extending in a first direction, light onto an object toward a second direction, the second direction crossing the first direction;

separating, by using a signal separator, optical signals, returning from the object, into a fluorescence signal and a non-fluorescence signal;

detecting, by using at least one first photodetector, the non-fluorescence signal;

detecting, by using at least one second photodetector, the fluorescence signal;

estimating at least one of a concentration or an amount of a first analyte in the object by analyzing the detected non-fluorescence signal; and estimating at least one of a concentration or an amount of a second analyte in the object by analyzing the detected fluorescence signal, wherein the separating comprises reflecting, by using a dichroic filter, an optical signal having a wavelength greater than a predetermined wavelength and passing an optical signal having a wavelength less than the predetermined wavelength, among the optical signals returning from the object, wherein the detecting the non-fluorescence signal comprises detecting, by using the at least one first photodetector, the optical signal, that is passed through the dichroic filter, as the non-fluorescence signal, the at least one first photodetector being a horizontal photodetector and extending in the first direction, wherein the detecting the fluorescence signal comprises detecting, by using the at least one second photodetector, the optical signal, that is reflected from the dichroic filter, as the fluorescence signal, the at least one second photodetector being a vertical photodetector and extending in the second direction, wherein a wall is provided on the substrate, the wall being positioned between the light source part and the signal separator and extending in the second direction, and the horizontal photodetector is provided on the substrate and contacting the wall, and wherein the signal separator further comprises a support configured to support the dichroic filter, the support being positioned between the dichroic filter and the wall and positioned on the horizontal photodetector.

16. The method of claim 15, wherein the first analyte comprises carotenoid; and the second analyte comprises flavonoid.

17. The method of claim 15, further comprising estimating at least one of a health condition or a life habit of the object based on the estimated at least one of the concentration or the amount of the first analyte and the estimated at least one of the concentration or the amount of the second analyte.

* * * * *